United States Patent
Kulesza et al.

(10) Patent No.: US 8,524,290 B2
(45) Date of Patent: Sep. 3, 2013

(54) NON-OCCLUDING NASAL MOISTURIZER AND METHODS OF USE

(76) Inventors: John E. Kulesza, Berlin, CT (US); Jeffrey Katz, San Francisco, CA (US)

( * ) Notice: Subject to any disclaimer, the term of this patent is extended or adjusted under 35 U.S.C. 154(b) by 0 days.

(21) Appl. No.: 13/277,310

(22) Filed: Oct. 20, 2011

(65) Prior Publication Data

US 2012/0100234 A1  Apr. 26, 2012

Related U.S. Application Data

(60) Provisional application No. 61/394,998, filed on Oct. 20, 2010.

(51) Int. Cl.
*A61K 36/00* (2006.01)
*A61K 36/87* (2006.01)

(52) U.S. Cl.
USPC .......................................... 424/725; 424/766

(58) Field of Classification Search
None
See application file for complete search history.

(56) References Cited

U.S. PATENT DOCUMENTS

| 5,472,684 A | * | 12/1995 | Nabi et al. ...................... 424/49 |
| 6,083,525 A | | 7/2000 | Fust |
| 6,228,347 B1 | | 5/2001 | Hersh |
| 6,544,530 B1 | * | 4/2003 | Friedman ...................... 424/400 |
| 7,001,603 B2 | | 2/2006 | Bagdi et al. |
| 7,393,548 B2 | | 7/2008 | Friedman |
| 7,439,269 B2 | | 10/2008 | Clarot et al. |
| 2008/0274163 A1 | * | 11/2008 | Schwartz et al. ............. 424/440 |
| 2010/0174000 A1 | | 7/2010 | Sarrazin et al. |

FOREIGN PATENT DOCUMENTS

WO  WO-2009/090558 A2  7/2009

OTHER PUBLICATIONS

Robert V. Petersen et al.; Studies on Nonaqueous Emulsions; J. Soc. Cosmetic Chemists, 19, pp. 627-640; (Aug. 19, 1968).
Tanja Hildenbrand et al.; Rhinitis Sicca, Dry Nose and Atrophic Rhinitis: A Review of the Literature; Springer; DOI 10.1007/s00405-010-1391-z; Sep. 29, 2010.
Neher et al.; Influence of Essential and Fatty Oils on Ciliary Beat Frequency of Human Nasal Epithelial Cells; 2008.
Miwa et al.; Measurement of Water Loss in Human Nasal Mucosa; 2006.
Masato Miwa et al.; Alteration of Epithelial Water Loss in Human Nasal Mucosa in Health and Disease; www.aro.org/archives/2006/2006_1202.html;2006.
Khairnar et al.; J. Am. Oil Chem. Soc., 2004; 81:505-10.

* cited by examiner

*Primary Examiner* — Qiuwen Mi
(74) *Attorney, Agent, or Firm* — Gifford, Krass, Sprinkle, Anderson & Citkowski, P.C.; Weston R. Gould

(57) ABSTRACT

Compositions are provided that provide improved nasal moisture, clarity, and lubrication. Compositions are oil-in-glycerin emulsions that include a surfactant promoting emulsification of a hydrophobic or otherwise water insoluble bioactive agent. The compositions are used in methods of promoting improved nasal moisture and reduction in nasal congestion.

7 Claims, 1 Drawing Sheet

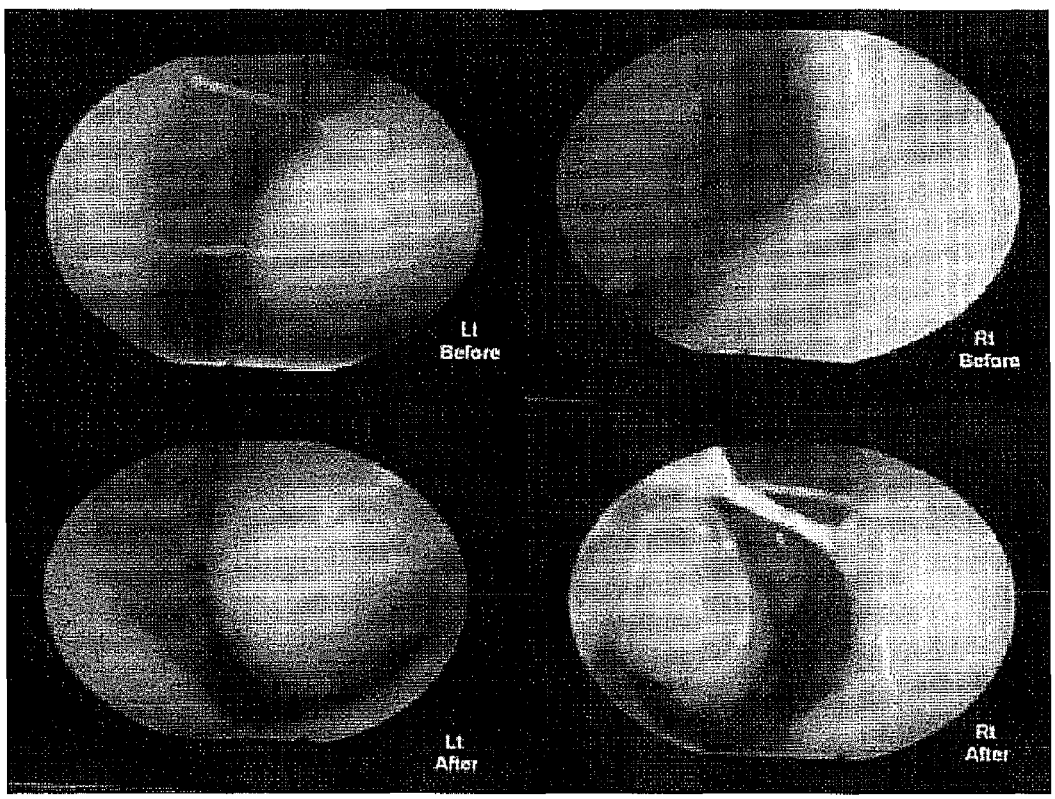

NON-OCCLUDING NASAL MOISTURIZER AND METHODS OF USE

CROSS REFERENCE TO RELATED APPLICATIONS

This application depends from and claims priority to U.S. Provisional Application No. 61/394,998 filed Oct. 20, 2010, the entire contents of which are incorporated herein by reference.

FIELD OF THE INVENTION

A nasal moisturizer that promotes proper nasal moisturization thus providing a more effective natural barrier against infection is provided whereby its application to the nasal mucosa delivers moisturizing components without occlusion.

BACKGROUND OF THE INVENTION

Nasal passages and other portions of the respiratory tract are lined with specialized tissue layers whose integrity and moisture balance provide effective blockade of infectious agents from entering the body. Proper moisturization of the respiratory tract, particularly the nasal passages also increases comfort and reduces risk of epistaxis.

The nasal mucosa is composed of several cell layers and cell types. Mucous cells are present throughout the nasal mucosa and are generally clustered into small glands that secrete a sticky substance called mucus. Mucus is composed of water, shed epithelial (surface) cells, dead leukocytes, mucin, and inorganic salts, among other things, that are all held in suspension.

Mucus functions as a trap for airborne particles (e.g., dust, bacteria, and viruses) that enter the nasal passages. The ciliated columnar epithelia function to remove trapped infectious agents, dust, and other debris trapped in the mucus from the nasal area, thus, protecting the body from developing illnesses. Mucus also lubricates the walls of the nose, sinuses, and throat.

Upper respiratory infections, acute or chronic allergy flare-ups of the nose, and acute or chronic non-allergic rhinosinusitis result in inflammation of the nasal mucosa. This inflammation commonly correlates with the presence of congestion that leads to discomfort and may result from increased blood flow swelling the nasal passages, fluid buildup in the nasal tissues, increased mucus viscosity, and depressed cilia activity. Further irritation may result from additional nasal drying due to subject intervention in attempt to reduce the congestion, the use of some medications, exposure to a low humidity environment, or simple dehydration from failure to consume sufficient fluids.

Thus, there is a need for a composition to increase nasal moisture without exacerbating or reducing cilia activity due to high viscosity to both improve moisturization of the nasal mucosa and reduce congestion.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Compositions are provided that promote improved nasal lubrication. These physiological improvements are accentuated when a subject is exposed to a dry environment for an extended period of time. The compositions also promote reduced epidermal water loss and improved ease in breathing. The improved nasal function provided by the compositions are believed to function in concert with one or more activities of a bioactive agent to improve nasal barrier function and prevention of transfer of infectious agents across the nasal epidermis.

Compositions are provided that include glycerin, one or more hydrophobic or otherwise water insoluble bioactive agents, and a non-ionic ethoxylated emulsifier that does not have a linkage to an aliphatic compound of greater than three carbons. The compositions optionally have a viscosity of less than 3000 centipoises. The compositions are optionally at least 50% by weight of the composition. A composition is optionally free of water or saline.

A bioactive agent is optionally an essential oil. Optional essential oils include those with one or more of various functional activities including topical anti-inflammatory activity, topical anti-fungal activity, topical anti-bacterial activity, topical antiparasitic activity, or topical anti-viral activity. Specific optional bioactive agents are *Vitis vinifera* seed oil, or tea tree oil.

The composition is provided as an oil in glycerin emulsion. The bioactive agent is optionally insoluble in glycerin as recognized in the art. To promote emulsification one or more emulsifiers are used, such as a copolymer emulsifier. An emulsifier optionally includes a polyoxyethylene. A copolymer is optionally a copolymer of ethylene glycol and propylene glycol. An emulsifier is optionally poloxamer 184.

One or more other components are optionally provided in a composition such as one or more humectants, illustratively hyaluronic acid or a salt of hyaluronic acid. A moisturizer is optionally included in a composition. An optional moisturizer is sodium PCA.

Also provided are methods of maintaining or improving the moisture or lubrication of the nasal mucosa. A method includes applying an inventive composition to the nasal mucosa such that the applying does not occlude the nasal mucosa, and wherein the composition is substantially free of saline. The composition is optionally applied at least once daily. Optionally, the composition is applied one or more times prior to anticipated exposure to a dry environment.

Methods of reducing nasal congestion in a subject are also provided. The methods illustratively include applying to the nasal mucosa an oil-in-glycerin emulsion consisting essentially of a hydrophobic bioactive agent, and a non-ionic ethoxylated emulsifier that is absent an aliphatic compound of greater than three carbons, and wherein said emulsion is non-occlusive to the nasal mucosa.

BRIEF DESCRIPTION OF THE DRAWINGS

FIG. 1 illustrates improved nasal lubrication in a human subject relative to a comparator following exposure of the subject to a dry environment.

DETAILED DESCRIPTION OF EMBODIMENTS OF THE INVENTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the process is described as an order of individual steps or using specific materials, it is appreciated that described steps or materials may be interchangeable such that the description of the invention includes multiple parts or steps arranged in many ways as is readily appreciated by one of skill in the art.

The invention has utility as nasal moisturizer and method of increasing nasal moisture, reducing congestion, and improving comfort. The oil-in-glycerin emulsions of the invention are pleasant for use on the skin and on mucous membranes such as the oral cavity, ears, nasal passages, and scalp. Additionally, the emulsions of the present invention are well accepted organoleptically and physiologically, hence, offering good patient compliance. The oil-in-glycerin emulsions are easy to apply, as well as being easy to remove after the substantial absorption thereof.

A composition based on an oil-in-glycerin emulsion is provided that when applied to the nasal mucosa increases moisture while not occluding the nasal passage or reducing ciliary activity. An oil-in-glycerin emulsion according to the present invention provides a stable storage and delivery vehicle for bioactive, water insoluble active ingredients, including plant derived oils. The oil-in-glycerin emulsion includes glycerin as a continuous phase of the emulsion. A plant oil, or other hydrophobic bioactive agent, is emulsified in glycerin by use of a non-ionic ethoxylated emulsifier. The emulsifier is free of aliphatic side chains or molecules such as fatty acids. The inventors have surprisingly discovered that stable oil-in-glycerin emulsions can be created without the need for an aliphatic linkage to an ethoxylated emulsifier. This improves the simplicity of the emulsion and allows ready delivery of bioactive agents to epithelial surfaces. As used herein the term "oil" in the term "oil-in-glycerin" emulsions means a hydrophobic or water insoluble bioactive agent and is not limited to bioactive agents that are oils.

As such, a composition as provided herein illustratively includes:
  a) glycerin optionally at 50 to 99.9 percent by weight;
  b) one or more non-ionic ethoxylated emulsifiers optionally at 0.01 to 50% by weight;
  c) one or more water insoluble bioactive agents optionally at 0.01 to 49% by weight.

Oil-in-glycerin emulsions are provided in which the water-insoluble bioactive agent is the internal phase and the glycerin is the external, continuous phase. The phase inversion ratio varies according to: emulsifier type; nature of the bioactive agent; temperature; and the various additives and variables chosen to support conditions for an oil-in-glycerin emulsion. Thus, the amount of emulsifier or emulsifiers should be adjusted to the internal oil volume ratio and more emulsifier is may be needed when a larger ratio of oily phase is present. Properly formulated oil-in-glycerin emulsions may contain up to equal parts of oil and glycerin phases. It is appreciated that a composition as provided herein optionally does not foam upon contact with skin or air.

The inventors discovered that a continuous phase that is glycerin is superior to other solvents in delivering an emulsified bioactive agent to the skin while simultaneously enhancing moisture, not occluding the skin or mucus membrane upon which it is applied, and maintaining or improving ciliary action such that a subject is left with a sense of decongestion and improved respiration through the nose. The use of glycerin as a hydrophilic solvent when used at concentrations at or in excess of 90%, 91%, 92%, 93%, 94%, 95%, 96%, 97%, 98%, 99%, 99.4%, or 99.6% by weight of a composition provides excellent viscosity for delivery of an active agent without dripping or running off vertical surfaces when applied, optionally without the use of additional agents to reduce or increase viscosity. As such, a composition with a final viscosity of 1,000 to 3,000 centipoises is optionally provided.

Sources of glycerin are known in the art such as Dow Chemical Co., Midland, Mich. Glycerin operable herein is optionally anhydrous, or contains less than 5 percent moisture. Optionally, glycerin is a 96% USP glycerin. Optionally, glycerin is a 99.5% USP glycerin. In some embodiments the glycerin is dehydrated such as by vacuum distillation or pervaporation such as that described by Khairnar and Pangarkar, *J. Am. Oil Chem. Soc.,* 2004; 81:505-10.

A bioactive agent is a hydrophobic, non-ionic, or water insoluble material. The bioactive agent may have anti-inflammatory, anti-bacterial, anti-parasitic, anti-viral, analgesic, immunity modulation and/or stress relaxant properties. Suitable active agents include but are not limited to active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, antiwrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, vasoconstrictors, vasodilators, vitamins, vitamin D derivatives, wound healing agents and wart removers. As is known to one skilled in the art, in some instances a specific active agent may have more than one activity, function or effect.

In some embodiments, the active agent is an anti-infective agent. Illustrative examples of an anti-infective agent include an antibiotic agent, an antibacterial agent, an antifungal agent, an agent that controls yeast, an antiviral agent and an antiparasitic agent. Exemplary anti-infective agents are beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quaternary ammonium compound, a biguanide, chlorohexidine, a triguanide, a bisbiguanide, a polymeric biguanide and a naturally occurring antibiotic compound, as well as analogs, derivatives, salts, ions and complexes thereof.

In particular embodiments, a bioactive agent is a plant oil. Plant oils include agar oil, ajwain oil, angelica root oil, anise oil, balsam oil, basil oil, bergamot oil, black Pepper essential oil, buchu oil, cannabis flower essential oil, caraway oil, cardamom seed oil, carrot seed oil, cedarwood oil, chamomile oil, cinnamon oil, cistus, citronella oil, clary Sage, clove leaf oil, coriander, costmary oil, cranberry seed oil, cumin oil/Black seed oil, cypress, davana oil, dill oil, eucalyptus oil, fennel seed oil, fenugreek oil, frankincense oil, galbanum, geranium oil, ginger oil, grapefruit oil, grape seed oil (e.g. *Vitis vinifera*), henna oil, jasmine oil, juniper berry oil, lavender oil, lemon oil, lemongrass oil, litsea cubeba oil, melissa oil (Lemon balm), mentha arvensis oil/Mint oil, mugwort oil, mustard oil, myrrh oil, neroli oil, orange oil, oregano oil, orris oil, parsley oil, patchouli oil, perilla essential oil, pennyroyal oil, peppermint oil, pine oil, rose oil, rosehip oil, rosemary oil, rosewood oil, sassafras oil, savory oil, schisandra oil, spearmint oil, star anise oil, tarragon oil, tea tree oil, thyme oil, vetiver oil, yarrow oil and ylang-ylang oil.

Methods of producing plant oils are known in the art illustratively by oil extraction or by pressing the seeds of a plant such as grape seeds, peanut seeds, or other seed. Many plant oils are available in the market and a person of ordinary skill in the art recognizes where to obtain them.

A bioactive agent is emulsified in a glycerin continuous phase by use of an emulsifier. An emulsifier is optionally a surfactant. A composition optionally includes up to 50% emulsifier. In some embodiments, an emulsifier is present at concentration equal to or in excess the concentration of bioactive agent. In some embodiments, an emulsifier is present at a weight percent that is at or less than 50%, 40%, 30%, 20%, 15%, 10%, 9%, 8%, 7%, 6%, 5%, 4%, 3%, 2%, 1%, 0.8%, 0.6%, 0.5%, 0.4%, 0.3%, 0.2%, or 0.1%. Emulsifiers operable in the present invention include copolymers. An emulsifier optionally includes a polyoxyethylene. In some embodiments an emulsifier is a copolymer of ethylene glycol and propylene glycol. Illustrative examples non-ionic ethoxylated emulsifiers include polaxamers typically sold under the tradename PLURONIC. Poloxamers are nonionic triblock copolymers composed of a central hydrophobic chain of polyoxypropylene (poly(propylene oxide)) flanked by two hydrophilic chains of polyoxyethylene (poly(ethylene oxide)). Many different polaxamers are known and available due to the ready customization of the polymer block lengths. Poloxamers are commonly named with the letter "P" (for Poloxamer) followed by three digits, the first two digits×100 give the approximate molecular mass of the polyoxypropylene core, and the last digit×10 gives the percentage polyoxyethylene content. For example, P407 is a Poloxamer with a polyoxypropylene molecular mass of 4,000 g/mol and a 70% polyoxyethylene content.

Poloxamers typically require combination with other hydrophobic agents such as fatty acids as taught by U.S. Pat. No. 6,544,530, or where the emulsion requires the poloxamer to be used with a supporting agent such as a surfactant as taught by WO/2009/090558. The present invention presents the unexpected finding that poloxamers alone, without supporting agents such as surfactants, binding to fatty acids or long (greater than three carbon) chain aliphatic molecules, or saccharide supports emulsification of oils or other hydrophobic bioactive agents in glycerin. As used herein an aliphatic molecule includes a carbon chain of three or more carbons.

A polaxamer is optionally a combination of two or more polaxamers. Typical examples of poloxamers include poloxamer 184, poloxamer 188, poloxamer 124, poloxamer 237, poloxamer 338, and poloxamer 407. A poloxamer is typically present in a composition at 0.1 to 15 percent by weight or any singular point or subdivision therebetween. A poloxamer is optionally present at 0.2 to 5 percent by weight, optionally, 0.1 to 1 percent by weight. In different embodiments the poloxamer includes a molecular weight in a range between about 2,000 to about 18,000 Da, or any value or range therebetween. Optionally, a poloxamer is of the molecular weight range from 2,000 and about 3,000; between about 6,800 and about 8,900; between about 7,600 and about 9,500; between about 9,800 and about 14,600; or between about 12,000 and about 18,000.

A composition optionally includes one or more non-ionic surfactants. A composition is optionally free of a surfactant other than one or more polaxamers. Illustrative examples of non-ionic surfactants include: polysorbates, such as polyoxyethylene (20) sorbitan monostearate (Tween 60) and poly (oxyethylene) (20), and sorbitan monooleate (Tween 80); poly(oxyethylene) (POE) fatty acid esters, such as Myrj 45, Myrj 49, Myrj 52 and Myrj 59; poly(oxyethylene) alkyl ethers, such as poly(oxyethylene) cetyl ether, poly(oxyethylene) palmityl ether, polyethylene oxide hexadecyl ether, polyethylene glycol ether, brij 38, brij 52, brij 56, brij W1, ceteareth 20; partial esters of sorbitol and its anhydrides such as sorbitan monolaurate and sorbitan monolaurate; mono or diglycerides; isoceteth-20; and sucrose esters among which are mono-, di- and tri-esters of sucrose with fatty acids. It is appreciated that when a surfactant is present in addition to an emulsifier such as a polaxamer that the surfactant is not covalently bound to the emulsifier.

A composition optionally includes one or more additives. It is appreciated, however, that a composition is optionally free of an additive. An additive illustratively is one or more antioxidants, anti perspirants, anti-static agents, buffering agents, bulking agents, chelating agents, cleansers, colorants, conditioners, deodorants, diluents, dyes, emollients, flavonoids, fragrances, hair conditioners, humectants, ionization agents, moisturizers, occlusive agents, perfuming agents, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers and vitamins. The source and type of additive operable herein is readily understood by one of skill in the art. Illustrative examples of additives are found in WO 2009/090558 and references cited therein.

A humectant (exclusive of glycerin), when included in a composition, helps retain moisture and also prevents rapid evaporation. Illustrative examples of humectants include propylene glycol and propylene glycol derivatives, guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, salts of hyaluronic acid, lactamide monoethanolamine, acetamide monoethanolamine and derivatives, esters, salts and mixtures thereof, as well as any suitable humectant found in Handbook of Pharmaceutical Additives published by Gower where one of ordinary skill in the art will recognize suitable humectants contained therein.

In some embodiments, one or more additional moisturizers are supplemented in the composition. Examples of additional moisturizers illustratively include allantoin, petrolatum, urea, lactic acid, sodium PCA, shea butter, caprylic/capric/stearic triglyceride, candelilla wax, propylene glycol, lanolin, hydrogenated oils, squalene, sodium hyaluronate and lysine PCA. Other examples may be found in the Handbook of Pharmaceutical Additives published by Gower.

Oil-in-glycerin emulsions are prepared as coarse or fine emulsions. Coarse oil-in-glycerin emulsions of 10 to 50 microns droplet size may be prepared by stirring. Droplet size may be controlled with appropriate mixing equipment and energy input. Fine oil-in-glycerin emulsions having a mean droplet size of less than 10 microns and are achieved with a conventional "Silverson" type mixer at moderate speed and a short duration of mixing. High speed "Silverson" type mixing is sufficient to obtain emulsions containing 500 to 3000 nanometers (0.5 to 3 microns) droplets. Further reduction of droplet size is possible by applying appropriate equipment of high pressure and high shear output.

It is appreciated that a composition is optionally free of mineral oil (Chemical Abstracts Service Registry number 8012-95-1) or petrolatum. It is recognized that petrolatum (VASELINE) forms an impermeable occlusive layer on the skin when applied. The prior art includes this material for the purpose of creating this occlusive layer as a way of protecting the skin and improving the penetration of active agents. (See WO 2009/090558.) The inventors unexpectedly discovered that the occlusive nature of petrolatum has unwanted side effects such as the result of inhalation of the material and reduction of ciliary action increasing the feeling of congestion. As such, a composition as provided herein is optionally free of a petrolatum.

Also provided are methods of moisturizing the nasal mucosa without significant occlusion thereof. Typical prior art moisturizers such as petroleum jelly prevent ciliary action leading to increased congestion. Also, unwanted side effects of inhalation of the petroleum product may occur. The processes provided involve applying an emulsion of water-insoluble bioactive agent in a glycerin continuous phase to the mucus membranes such as those present in the nasal cavity. This process reduces the possibility of unwanted inhalation and does not significantly alter the ciliary action of the membrane. Thus, an inventive process creates a decongesting feeling in a subject though the simultaneous long lasting moisturizing properties and decongesting properties of the applied composition.

As used herein the term "subject" refers to a human, non-human primate, pig, bovine, equine, mouse, rat, guinea pig, rabbit, hamster, or other mammal.

Also provided is a process of preventing the ability of an infectious agent from entering a subject or reducing a subject's susceptibility to an infectious agent by applying an oil-in-glycerin emulsion of the invention illustratively where the oil is a hydrophobic or water insoluble bioactive agent that acts as an anti-infective. Additional protection is provided by simple moisturizing the nasal mucosa such that its rupture is less likely and its function is maintained so that infectious agents are less likely to cross the membrane and infect a subject.

Various aspects of the present invention are illustrated by the following non-limiting examples. The examples are for illustrative purposes and are not a limitation on any practice of the present invention. It will be understood that variations and modifications can be made without departing from the spirit and scope of the invention. A person of ordinary skill in the art readily understands where reagents and apparatuses necessary to practice the invention may be obtained.

EXAMPLE 1

Formation of an oil-in-glycerin emulsion. Two phases are created. Phase A contains Glycerin USP 96% obtained from Dow Chemical placed in a suitably sized kettle and maintained at approximately 25° C. In a separate kettle also at 25° C., a Phase B solution is created where equal parts of Polaxamer 184 (PLURACARE L-64) (BASF) is mixed with *Vitis vinifera* (Grape) Seed Oil (Arista Industries, Wilton, Conn.) using a propeller mixer without vortexing until a smooth uniform mixture is created.

The Phase B solution is then gently mixed with the Phase A solution until a uniform mixture is obtained. The resulting mixture may further clarify upon standing at room temperature for 24 hours. The resulting emulsion is stored at ambient temperature in a polyethylene lined container protected from light.

The resulting formulation contains:

| Ingredient | Weight Percent |
|---|---|
| Glycerin USP 96% | 99.6% |
| Polaxamer 184 | 0.2% |
| *Vitis vinifera* (Grape) Seed Oil | 0.2% |

EXAMPLES 2-11

The emulsion of Example 1 is created replacing the grape seed oil with one of the following at 0.2% final weight percent: 2) balsam oil; 3) *Eucalyptus radiata* essential oil; 4) evening primrose oil; 5) lavender essential oil; 6) meadowfoam seed oil; 7) ravensara essential oil; 8) tea tree oil; 9) spearmint essential oil; 10) sweet almond oil; or 11) chamomile essential oil.

EXAMPLE 12

The emulsion of Example 1 is subjected to viscosity testing using a Brookfield DV-1 continuous sensing Digital Viscometer from Brookfield Engineering Laboratories, Inc., Middleboro, Mass. A T-E spindle is used at 0.3 RPM for 1 minute. The resulting emulsion has a viscosity of 1,000-2,000 cPs.

EXAMPLE 13

The composition of Example 1 is used in a study of nasal moisture. Twenty consenting adults participate in a single-blind trial. Prior to delivery of test composition, the inferior nasal concha is photographed via a nasal endoscope. Each subject is provided the composition of Example 1 in one nostril (chosen at random) administered on the end of a cotton swab, while the other nostril is treated with a dry swab that was placed in a freezer for a short time as a control. The cold control swab felt to the subject indistinguishable from the swab applying the composition of Example 1. Each subject is then exposed to a low humidity environment that consisted of placement in front of a hot hair dryer that blew directly into the face for fifteen minutes. The subjects place moisturizer on their lips and wear goggles to prevent drying of the lips and eyes, respectively. Subjects are instructed to breath via the mouth only during the exposure period.

At the end of the exposure period, each subject are asked to complete a questionnaire regarding the ease of breathing out of each nostril and the relative moisture of each nostril. All subjects answer that the nostril treated with the composition of Example 1 both provides greater ease in breathing as well as better lubrication and comfort.

Each nostril is also photographed by a nasal endoscope immediately at the end of the test period. The results from one subject are illustrated in FIG. 1. The nostril treated with control composition (left) demonstrates increased dryness and raw appearance. The right nostril treated with the composition of Example 1 demonstrates superior lubrication. These studies demonstrate that the composition of Example 1 provides improved nasal lubrication and ease of breathing when a subject is exposed to a dry environment.

EXAMPLE 14

The ability of the composition of Example 1 to prevent transepidermal water loss of the nasal epithelium is determined in subjects relative to the comparators physiological saline (0.9%), 10% NaCl solution, and water. A single nostril is administered the test composition of Example 1 or a comparator solution, and transepidermal water loss is measured using an evaporation meter (TEWAMETER 300; Courage+ Khazaka electronic GmbH, Germany) using the original probe. Subjects are positioned in a seated posture and hold their breath during measurements. Basal measurements are performed prior to application of a test composition.

After application of physiological saline, water loss is observed at a slight decrease. After application of 10% NaCl, water loss is significantly increased compared with basal state. Little change is observed in nostrils treated with water. The composition of Example 1, however, produces a significant decrease in transepidermal water loss. These studies demonstrate improved ability to retain moisture in the nasal epithelium of subjects administered the composition of Example 1.

The study is repeated using the compositions of Example 2. Similar to the results of the compositions of Example 1, the compositions of Example 2 show reduced water loss relative to comparator compositions and the basal state.

Various modifications of the present invention, in addition to those shown and described herein, will be apparent to those skilled in the art in view of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A method of moisturizing the nasal mucosa comprising:
    applying to the nasal mucosa a composition comprising:
    glycerin;
    a bioactive agent; and
    a non-ionic ethoxylated emulsifier, said emulsifier absent a linkage to an aliphatic compound of greater than three carbons;
    wherein said applying does not occlude the nasal mucosa, and wherein said composition is substantially free of saline or water; and
    moisturizing said nasal mucosa.

2. The method of claim 1 further comprising reducing susceptibility to infectious agents by application an anti-infective included in said composition.

3. The method of claim 1 wherein said applying is at least once daily.

4. The method of claim 1 where said bioactive agent is *Vitis vinifera* seed oil, balsam oil, *Eucalyptus radiata* essential oil, evening primrose oil, lavender essential oil, meadowfoam seed oil, ravensara essential oil, tea tree oil, spearmint essential oil, sweet almond oil, or chamomile essential oil.

5. A method of reducing nasal congestion in a subject comprising:
    applying to the nasal mucosa an oil-in-glycerin emulsion consisting essentially of a hydrophobic bioactive agent, and a non-ionic ethoxylated emulsifier, said emulsifier absent an aliphatic compound of greater than three carbons; said emulsion substantially free of water,
    wherein said emulsion is non-occlusive to the nasal mucosa and
    reducing nasal congestion in said subject.

6. The method of claim 5 wherein said applying is at least once daily.

7. The method of claim 5 where said bioactive agent is *Vitis vinifera* seed oil or tea tree oil.

* * * * *